| United States Patent [19] | [11] | 4,022,199 |
|---|---|---|
| Fetty | [45] | May 10, 1977 |

[54] METHOD OF PREVENTING THE SPREAD AND CONTROL OF MASTITIS

[76] Inventor: Walter W. Fetty, 1218 Central Ave., Nebraska City, Nebr. 68410

[22] Filed: Sept. 24, 1975

[21] Appl. No.: 616,323

[52] U.S. Cl. .............................. 128/132 R; 128/157
[51] Int. Cl.$^2$ .......................................... A61F 13/00
[58] Field of Search .......... 128/132, 1 R, 260, 157; 119/1, 146, 158

[56] References Cited

UNITED STATES PATENTS 2,604,092    7/1952    Brown et al. .................. 128/132 R
2,824,559    2/1958    Sullivan ............................ 128/157

OTHER PUBLICATIONS

Milks Vet. Pharm., Mat. Medica & Therapeutics, 1949, pp. 605–607.

Primary Examiner—Lawrence W. Trapp
Attorney, Agent, or Firm—Henderson, Strom & Sturm

[57] ABSTRACT

A method of preventing the spread and control of mastitis by applying a liquid coating to the animals' teats. The liquid coating dries and forms a pliable protective film on the teat thereby preventing mastitis bacteria from entering the milk canal of the animals' teats.

2 Claims, No Drawings

METHOD OF PREVENTING THE SPREAD AND CONTROL OF MASTITIS

BACKGROUND OF THE INVENTION

In the milk producing industry animal diseases are of constant concern. A serious disease which is common among milk producing animals is mastitis. Mastitis is a bacterial disease and may easily be spread throughout a herd of livestock from a single infected animal. Mastitis effects the ability of the milk producing animal to give milk and is spread between animals by the mastitis bacteria contacting a healthy animal and traveling up the milk canal of the animal.

Typical of the steps taken to control and prevent the spreading of mastitis is the type of procedure discussed in U.S. Pat. No. 3,648,696 to Keith. Keith, while directly concerned with the apparatus involved in the procedure, demonstrates the use of antiseptic solutions and suspensions. The procedure discussed in Keith is excellent for disinfecting purposes during the actual milking process; however, it does not provide a suitable solution to the control and isolation of the mastitis bacteria.

The actual sreading of the mastitis bacteria from an infected animal to a healthy animal normally would not occur during the milking process because of the strict sanitary conditions present. Instead, the actual spreading of the mastitis bacteria occurs as the infected animals mingle with the healthy animals in the field. Further, the bacteria may be carried by flying insects as they move about a group of animals. Another common method of spreading the bacteria occurs when the bacteria drops from an infected animal, perhaps while walking or grazing and comes into contact with a healthy animal. This method of infecting healthy animals is common when viewed in light of the characteristics of livestock. Typically, cattle walk single file on a worn path to and from the field to the milking buildings. Some bacteria drops off the infected animal into heavy grass only to re-attach itself to another animal coming into contact with it.

Therefore, between the disinfecting process that occurs at each milking, there is a good chance of healthy animals coming into contact with the bacteria and obtaining mastitis. Thus, there is a need for a method of preventing healthy livestock from contracting the mastitis bacteria from infected animals.

The most obvious solution would be isolating the infected animal. However, by the time an infected animal is diagnosed, the bacteria may be spread to several other animals in the herd. Further, complete isolation of one or more animals to the degree of preventing insects from frequenting the animal would be for all practical purposes impossible for a farmer.

SUMMARY OF THE INVENTION

The above and other disadvantages of prior methods of preventing the spread of mastitis between livestock are overcome by coating the teats of the animal with a liquid mucilage gum. The gum dries quickly, forming a pliable, flexible film. The film will prevent the mastitis bacteria from entering the milk canal, thus preventing the animal from being infected with mastitis. The mucilage gum is applied immediately after milking and may be peeled off of the animal before milking again.

It is thus an object of the invention to provide a method for the control of mastitis.

A second object of the present method is to prevent healthy animals from being infected with mastitis bacteria from infected animals.

A third object of the invention is to develop a method for the control of mastitis which is simple and easy to use by the farmer.

A further object of the present invention is to provide a method for the control of mastitis which does not cause discomfort to the animal and does not interfere with the normal milking of the animal.

Other objects, advantages and novel features of the invention will become apparent from the description of the invention.

DESCRIPTION OF THE PREFERRED EMBODIMENT

A liquid mucilage gum is applied to the lower portion of the milk producing animals' teats. The mucilage gum may either be sprayed, brushed or dipped onto the animal. The only requirement being to cover completely the lower portion of the animals' teats to insure a covering over the opening to the milk canal. The mucilage gum applied as a liquid, when exposed to the air, will dry and form a pliable, flexible film over the skin. When dry, the film will prevent harmful bacteria, including that of mastitis, from entering the milk canal of the teat and causing an infection therein. Further, the coating if applied to infected animals will prevent the bacteria from leaving the animal through its milk canal, thus reducing the risk of contamination of the healthy animals.

The liquid would normally be applied after the milking of the animal is completed and before it is turned out from the barn to mingle with the other animals. When it is time to milk the animal again, the film layer is merely peeled off from the skin.

The mucilage gum liquid is available commercially from several manufacturers and is comprised of the following ingredients: water, SD alcohol 40, polyvinyl alcohol, propylene glycol, PPG-28 Cetyl ether and methylparaben.

Obviously, many modification and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A method of preventing the spread of mastitis bacteria among milk producing animals, comprising the steps of:
   a. providing a quantity of liquid mucilage gum comprising water, SD alcohol 40, polyvinyl alcohol, propylene glycol, PPG-28 Cetyl ether and methylparaben;
   b. applying a substantially uniform coating of said liquid mucilage hum on the animals teats and milk canal; and
   c. drying said mucilage gum to thereby form a pliable protective film thereon to prevent mastitis bacteria from intering the milk canal of healthy animals and from leaving the body of infected animals.

2. The method of claim 1 further including the steps of:
   d. removing said protective film from the animals teats;
   e. extracting milk through the teats; and
   f. repeating steps (b) and (c) above to form a protective film on the teats.

* * * * *